United States Patent
Robertson et al.

(10) Patent No.: US 11,026,663 B2
(45) Date of Patent: Jun. 8, 2021

(54) ULTRASOUND IMAGING APPARATUS AND METHODS

(71) Applicant: IMV Imaging (UK) Ltd., Bellshill (GB)

(72) Inventors: Robert Robertson, Bellshill (GB); John Fothergill, Bellshill (GB)

(73) Assignee: IMV IMAGING (UK) LTD, Bellshill (GB)

( * ) Notice: Subject to any disclaimer, the term of this patent is extended or adjusted under 35 U.S.C. 154(b) by 550 days.

(21) Appl. No.: 15/907,642

(22) Filed: Feb. 28, 2018

(65) Prior Publication Data

US 2018/0242955 A1     Aug. 30, 2018

(30) Foreign Application Priority Data

Feb. 28, 2017    (GB) ..................................... 1703254

(51) Int. Cl.
*A61B 8/00*      (2006.01)
*A61B 8/08*      (2006.01)
*A61B 8/14*      (2006.01)

(52) U.S. Cl.
CPC ............... *A61B 8/56* (2013.01); *A61B 8/145* (2013.01); *A61B 8/4427* (2013.01); *A61B 8/4472* (2013.01); *A61B 8/5207* (2013.01)

(58) Field of Classification Search
CPC ......... A61B 8/56; A61B 8/5207; A61B 8/145; A61B 8/4427; A61B 8/4472; A61B 8/565; H04N 19/134; H04N 19/172; H04N 19/174; H04N 19/189

See application file for complete search history.

(56) References Cited

U.S. PATENT DOCUMENTS

| | | |
|---|---|---|
| 2003/0181811 A1 | 9/2003 | Amemiya et al. |
| 2007/0065033 A1 | 3/2007 | Hernandez et al. |
| 2010/0202510 A1 | 8/2010 | Kyle |
| 2010/0305449 A1* | 12/2010 | Wegener ............ G01S 7/52034 600/459 |
| 2010/0331689 A1* | 12/2010 | Wegener .................. A61B 8/06 600/443 |
| 2011/0222791 A1* | 9/2011 | Mansour ............. G01S 7/52034 382/240 |
| 2014/0357993 A1 | 12/2014 | Hiriyannaiah et al. |
| 2015/0087987 A1 | 3/2015 | Ryu et al. |
| 2016/0055305 A1 | 2/2016 | Hiriyannaiah et al. |
| 2017/0143313 A1* | 5/2017 | Pelissier ................. A61B 8/461 |
| 2017/0242112 A1* | 8/2017 | Liu ........................ G01S 7/5208 |

* cited by examiner

*Primary Examiner* — Joel Lamprecht
(74) *Attorney, Agent, or Firm* — Fox Rothschild LLP (57) ABSTRACT

Ultrasound imaging apparatus and method for veterinary applications. An ultrasound probe obtains ultrasound frame data which is compressed prior to wireless communication to a data processing unit. The data processing unit decompresses the ultrasound frame data and uses it to generate ultrasound images. The transmit bandwidth or transmit buffer size are monitored and the scan rate is reduced if required to maintain low latency. The apparatus generates images with lower latency and greater tolerance of variations in wireless data transfer bandwidth than where images are generated by an ultrasound probe and transmitted wirelessly to a remote display. A regularly updated image can be displayed even if image quality may be temporarily reduced.

20 Claims, 4 Drawing Sheets

ULTRASOUND IMAGING APPARATUS AND METHODS

FIELD OF THE INVENTION

The invention relates to the field of ultrasound imaging apparatus and methods for medical, particularly veterinary, ultrasound imaging. The apparatus comprises an ultrasound scanner which makes ultrasound signal measurements and a separate ultrasound data processor which generates real-time images.

BACKGROUND TO THE INVENTION

It is known to provide ultrasound scanners for veterinary use which generate streaming video data, in a format such as MPEG, and which transmit that video data wirelessly, for example though a W-iFi connection, to a separate display device, such as a dedicated ultrasound display device, smart phone, or tablet, to enable a user to view the scanned tissue in real time. They are typically handheld or at least have a handheld probe.

Veterinary ultrasound scanners are often used in challenging environments, for example outdoors, or in farm buildings. Environmental factors (such the presence of walls, metal objects etc.), combined with movement of both the scanner and the display device mean that Wi-Fi data transmission speed and reliability may well be substantially below which can be achieved in optimum conditions and may vary intermittently. This can lead to poor quality image transmission, for example, video may suffer a drop in quality, freeze, or be lost.

Another problem arising from limitations in Wi-Fi data transmission speed and reliability is that of a high latency, i.e. a high time delay/lag between ultrasound data sampling and display of the resulting image. Even a latency of 0.25 seconds, for example, substantially reduces the utility of a handheld ultrasound scanner.

Known handheld scanners with wireless data transmission interfaces typically generate images in an MPEG format. By an MPEG format we refer to a format approved by the Moving Pictures Expert Group, including but not limited to MPEG-1 (ISO/IEC 11172), MPEG-2 (ISO/IEC 13818), MPEG-4 (ISO/IEC 14496), MPEG-7 (ISO/IEC 15938), MPEG-21 (ISO/IEC 21000). MPEG and similar formats compress images in a "group of pictures" or GOP structure, which are effectively a collection of consecutive images in a coded video stream. Each group of pictures is encoded using intra frame and inter frame compression techniques and the compressed data structure includes I frames (intra coded picture frames) which are effectively reference frames, coded independently of other pictures, as well as other frames (P frames and B frames) which include motion-compensated information about differences between consecutively decompressed pictures. The inventors have found that when using MPEG and other image compression formats with a GOP structure is that there is inherently a significant latency arising from the need to store each of the group of pictures before they can be encoded and transmitted. The number of pictures which are included in a single group is known in the art as the GOP size, or GOP length and is typically at least 6, and often more in order to facilitate better compression (e.g. 12, 15 or 18). The latency introduced by encoding in MPEG or another format using a group of pictures structure can present a significant reduction in ease of use in real-time ultrasound scanning, particularly in veterinary applications where the hand and probe cannot be visualised and the operator must rely solely on ultrasound imaging for probe positioning. This cannot be readily overcome by increasing sampling rate as that would both increase power consumption and fail where bandwidth was limited.

The invention seeks to address one or more of the problems set out above.

SUMMARY OF THE INVENTION

According to a first aspect of the invention there is provided (e.g. veterinary) ultrasound imaging apparatus comprising an ultrasound scanner and a separate ultrasound data processor:
the ultrasound scanner comprising:
one or more ultrasound sources and receivers,
transmit circuitry configured to apply electrical signals to the ultrasound sources to transmit ultrasound pulses into a scan region,
receive circuitry configured to measure ultrasound echoes received at the ultrasound receivers from the scan region,
a beam processor configured to process the measured ultrasound echoes and output ultrasound frame data, the ultrasound frame data comprising measurements of ultrasound echoes from each of a series of scan positions in the scan region,
a data compressor configured (e.g. programmed) to process ultrasound frame data output by the beam processor to generate compressed ultrasound frame data, and
a wireless transmitter configured to wirelessly transmit the compressed ultrasound frame data;
the ultrasound data processor comprising:
a wireless receiver configured to receive the compressed ultrasound frame data transmitted by the wireless transmitter,
a data decompressor configured to decompress compressed ultrasound frame data received by the wireless transmitter,
an image processor configured to process decompressed data output by the data decompressor to form ultrasound images of the scan region, and
a display interface (and typically also a display, although the display interface may be a video data output interface, for use with a separate display) configured to output the ultrasound images formed by the image processor.

The invention extends in a second aspect to a method of processing ultrasound echo data to form images (e.g. of a region of a non-human animal), the method comprising:
at an ultrasound scanner comprising one or more ultrasound sources and receivers, receiving ultrasound echoes from a scan region,
processing measurements of the received ultrasound echoes to thereby calculate ultrasound frame data, the ultrasound frame data comprising measurements of ultrasound echoes from each of a series of scan positions in the scan region,
compressing the ultrasound frame data to generate compressed ultrasound frame data,
transmitting the compressed ultrasound frame data through a wireless transmitter to a wireless receiver of an ultrasound data processor,
at the ultrasound data processor, decompressing the received ultrasound frame data, processing the decompressed data to form ultrasound images of the portion of the subject, and outputting the ultrasound images (for example displaying the ultrasound image or outputting video data through an interface).

The method typically also comprises controlling transmit circuitry to apply electrical signals to the ultrasound sources to transmit ultrasound pulses into the scan region (thereby leading to said ultrasound echoes from the scan region).

Accordingly, the ultrasound frame data is compressed prior to being transmitted through a wireless communications channel comprising the wireless transmitter and the wireless receiver. The compressed ultrasound frame data is then decompressed and used to generate images. This enables reduced latency in comparison to known ultrasound scanners which generate video images using MPEG or another group of pictures compression technique. The ultrasound images are typically presented as video images.

The wireless transmitter and receiver are typically radio transmitters and receivers. Typically, they are radio transceivers. It may be that the wireless transmitter and receiver are Wi-Fi transmitters and receivers (e.g. Wi-Fi transceivers). Thus, the compressed data may be transmitted by Wi-Fi. Wi-Fi is a wireless radio transmission protocol specified by the IEEE 802.11 standards. (Wi-Fi is a trade mark of the Wi-Fi Alliance).

The invention is particularly relevant when the compressed data is transmitted by Wi-Fi. Wi-Fi is convenient to use as it is found in many common computing devices but Wi-Fi can have varying and unreliable bandwidth when implemented outdoors or in other field sites typical in veterinary applications. The invention improves image quality and/or reduces latency.

The measurements of ultrasound echoes from each of a series of scan positions in the scan region typically comprise data (samples) specifying the measured strength of ultrasound echoes received by one or more ultrasound receivers from the corresponding position within the scan region. By the strength of ultrasound echoes we refer to a parameter relating to the intensity, amplitude or brightness of the ultrasound echoes, in absolute terms or relative to the incident ultrasound pulses.

The transmit circuitry is typically also configured to focus transmitted ultrasound pulses on each of the plurality of scan positions in the scan region in turn. Typically, transmitted ultrasound pulses radiate along a narrow beam and thereby reach a plurality of scan positions along a scan line in turn. The person skilled in the art is familiar with beam processors capable of focussing transmitted ultrasound pulses on specific position in a scan region and beam processors capable of processing the output of ultrasound receivers to determine the measured strength of echoes received from specific scan positions.

Typically, the ultrasound scanner comprises an ultrasound probe region (for example an ultrasound probe), the ultrasound probe region comprising the one or more ultrasound sources and receivers. The one or more ultrasound sources and receivers may be an array of ultrasound sources and receivers. The array of ultrasound sources and receivers is typically in the form of a one dimensional array, for example spaced apart along a linear or curved line. However, it is possible that the one or more ultrasound sources and receivers is mounted on a support and is swept repetitively along a path in use. In this case a single ultrasound source and a single ultrasound receiver (e.g. a single ultrasound transceiver) may be sufficient.

The scan region is typically planar (being a cross-section through a region of a subject, in use). The scan region is typically defined by the configuration of the ultrasound sources and receivers, and the transmit circuitry and beam processor.

The transmit circuitry is typically configured to focus transmitted ultrasound pulses on a plurality of scan positions in the scan region in turn (typically a plurality of scan lines which are scanned in turn, each having a plurality of spaced apart scan positions which are scanned in turn as ultrasound pulses focussed on the scan line pass into the tissue). The person skilled in the art is familiar with beam processors capable of focussing transmitted ultrasound pulses on specific lines in a scan region and beam processors capable of processing the output of ultrasound receivers to determine the measured strength of echoes received from specific scan positions.

The scan region is typically scanned as a series of scan lines, extending from the ultrasound probe region (i.e. from the array one or more ultrasound transmitters and receivers, or the path along which one or more ultrasound transmitters and receivers are repetitively swept, where appropriate) at different angles. The plurality of scan positions in the scan region typically comprises a plurality of scan positions spaced apart (usually regularly) along each of a plurality of scan lines which extend through the scan region at different angles relative to the ultrasound probe region (i.e. from the array of ultrasound transmitters and receivers, or the path along which one or more ultrasound transmitters and receivers are repetitively swept, where appropriate).

The ultrasound frame data typically comprises ultrasound line data portions which specify the measured strength (e.g. intensity or amplitude) of ultrasound echoes received by one or more ultrasound receivers from a series of spaced apart positions along a line (typically a straight line extending from the ultrasound probe region into the scan region). Typically, the ultrasound frame data comprises a plurality of ultrasound line data portions each of which relates to a different line extending into the scan region and which have been measured consecutively. Typically each relates to a line extending at a different angle from the ultrasound probe region into the scan region. Typically, the lines extend at different angles in the same plane. Typically the lines are in a cross-section through a region of the subject, in use.

Typically, the ultrasound frame data is divided into ultrasound frames, each of which represents measurements of ultrasound echoes across the scan region, suitable for forming an image frame. In this case, each ultrasound frame comprises a plurality of ultrasound line data portions extending through the scan region, e.g. at different angles relative to the ultrasound probe region (i.e. the array of ultrasound sources and receivers, or the path along which one or more ultrasound transmitters and receivers are repetitively swept, as appropriate). It is not however necessary for each ultrasound frame portion to have ultrasound line data portions relating to the same angles relative to the ultrasound probe, for example, ultrasound line data portions relating to different scan lines (angles relative to the ultrasound prove region/array of ultrasound sources and receivers, or the path along which one or more ultrasound transmitters and receivers are repetitively swept, where appropriate) may be included in alternate ultrasound frame data structures.

By an ultrasound image we refer to a visual representation, in at least two dimensions, of the scan region as indicated by the ultrasound echoes which are received by the at least one ultrasound receiver, in response to ultrasound signals being generated by the at least one ultrasound transmitter. The ultrasound images are typically frames of video images. The ultrasound images are typically pixelated, for example two dimensional pixelated images. The pixels typically represent parts of the image in a rectangular array. In the present invention, the ultrasound images are obtained by processing ultrasound frame data which has been compressed, transmitted wirelessly, and decompressed. Typically, the processing of the decompressed image data to form an ultrasound image comprises scan conversion. The processing of the decompressed image data to form an ultrasound image may comprise one or more of: angle compounding, frame smoothing and boundary detection. The image processor may comprise a scan converter. The image processor may comprise one or more of: an angle compounder, a frame smoother and a boundary detection module.

The data compressor is preferably configured to compress each ultrasound frame of ultrasound frame data separately. The data compressor is preferably configured to output compressed ultrasound frame data in which each individual ultrasound frame is compressed independently of any other frame. Data compression preferably comprises processing individual ultrasound frames separately. Data compression preferably generates data portions each of which represents an individual ultrasound frame without reference to any other frame. This contrasts with group of picture type data compression techniques which output data representing differences between consecutive images/frames (along with reference frames).

The data compressor may be configured to compress each individual ultrasound line data portion separately. The data compressor may output compressed ultrasound frame data in which each individual ultrasound line is compressed separately. Data compression may comprise processing individual line data portions separately. Data compression may generate data portions each of which represents an individual ultrasound line data portion without reference to any other ultrasound line data.

By compressing each ultrasound frame, and in some embodiments each ultrasound line, separately, latency can be reduced. Furthermore, in some embodiments introduced below in which in some circumstances the scan rate or bandwidth of transmitted data is selectively reduced, this can be done without delay as frames (or lines respectively) need not each have the same size.

The ultrasound frame data may comprise ultrasound line data portions which specify the measured strength of ultrasound echoes received by one or more ultrasound receivers from a series of spaced apart position along a line. The data compressor may be configured to output compressed ultrasound frame data in which each individual ultrasound line is compressed separately and/or wherein the data compressor is configured to calculate and encode the differences between consecutive measurements within ultrasound line data portions The data compressor may be a variable length code compressor. The data compressor may be configured to calculate and encode the differences between consecutive measurements within ultrasound line data portions. The step of compressing the ultrasound frame data may comprise applying a variable length code compression algorithm to the ultrasound frame data. Typically, the method comprises calculating the difference between measurements (typically consecutive measurements) of the strength of ultrasound echoes within ultrasound data lines and encoding these differences, for example using a variable length code. Using a variable length code typically comprises selecting, from amongst a group of codes, which includes codes of a plurality of different bit lengths, a code representative of the respective difference. We have found that variable length codes are efficient for compressing ultrasound line data.

The ultrasound scanner may be configured to regulate (e.g. reduce) the number of scan positions per unit of measurement time of the ultrasound frame data which is transmitted by the wireless transmitter, in compressed form, typically responsive to a received variable relating to a transmission property of the wireless transmitter. The method may comprise receiving a variable relating to a transmission property of the wireless transmitter and varying (e.g. reducing) the number of scan positions per unit of measurement time of the ultrasound frame data which is transmitted by the wireless transmitter, in compressed form, responsive thereto.

We refer to the number of scan positions per unit of measurement time in respect of which data is transmitted (in compressed form) because this determines the rate at which data for transmission accumulates.

The transmission property of the wireless transmitter may be related to the current transmission bandwidth of the wireless transmitter. The transmission property of the wireless transmitter may be related to the current delay between data being queued for wireless transmission and the data being transmitted, for example, a parameter related to the amount of data in a transmit buffer of the wireless transmitter (for example a measurement of the amount of data in the transmit buffer, or the spare capacity of a transmit buffer (of defined size), or the estimated time until the buffer has a certain amount of data stored therein, e.g. is full).

It may be that the number of scan positions per unit of measurement time of the ultrasound frame data is reduced responsive to detection that the amount of data in the transmit buffer exceeds a threshold.

It may be that the variable relating to the transmission capacity of the wireless transmitter is a time-varying parameter indicative of the current transmission bandwidth of the wireless transmitter to the wireless receiver.

The number of scan positions per unit of measurement time in respect of which compressed ultrasound frame data is transmitted may be regulated (e.g. reduced) by reducing the number of scan positions per unit of measurement time in respect of which compressed ultrasound frame data is transmitted, for example, by one or more of:

regulating (e.g. reducing) the number of scan positions per scan line in respect of which compressed ultrasound frame data is transmitted;

regulating (e.g. reducing) the number of scan lines per ultrasound frame in respect of which compressed ultrasound frame data is transmitted;

regulating (e.g. increasing) the period (of measurement time) between ultrasound frames in respect of which compressed ultrasound frame data is transmitted.

This enables the number of scan positions per unit of measurement time in respect of which data which is transmitted to be varied rapidly in response to changing properties of the transmission of data wirelessly. Thus, if there is a decrease in available bandwidth, or an increase in the amount of data queued in the buffer for transmission, the amount of data per unit of measurement time which is transmitted can be reduced, so that the available bandwidth is sufficient to transmit the resulting compressed data and/or the size of the buffer is reduced.

It is better to reduce the number of scan positions in respect of which ultrasound frame data is transmitted, which may cause a degradation of image quality, than to lose continuity of image formation and output. Accordingly, preferably, in at least some circumstances reducing the number of scan positions in respect of which ultrasound frame data is transmitted leads to some degradation of image quality (e.g. resolution and/or frame rate) but without a break in ultrasound image formation and output.

It may be that the number of scan positions per unit of time in respect of which compressed ultrasound frame data is transmitted is regulated (e.g. reduced) progressively through a plurality of different modes, which differ in terms of the number of scan positions in respect of which compressed ultrasound frame data is transmitted, in a predetermined order, the modes differing in terms of one or more of: the number of scan positions per scan line, the number of scan lines per ultrasound frame and/or the period between ultrasound frames. It may be that the apparatus is configured to vary the number of scan positions per unit of measurement time in respect of which data is transmitted within an ultrasound frame.

It may be that the number of scan positions per unit of measurement time in respect of which compressed ultrasound frame data is transmitted is varied (e.g. reduced) progressively (responsive to measurements of the variable relating to a transmission property of the wireless transmitter) through a plurality of different modes, which differ in terms of the number of scan positions in respect of which compressed ultrasound frame data is transmitted, in a predetermined order. The modes may differ in terms of one or more of: the number of scan positions per scan line, the number of scan lines per ultrasound frame and/or the period between ultrasound frames.

The number of scan positions per unit of measurement time in respect of which data is transmitted may be varied within an ultrasound frame. For example, the number of scan positions per scan line in respect of which compressed ultrasound frame data is transmitted may change during an ultrasound frame. The angular spacing between scan lines in respect of which compressed ultrasound frame data is transmitted may change during an ultrasound frame. Thus, it may be that not only can the number of scan positions per scan line and/or the number of scan lines per ultrasound frame/ angular spacing between scan lines change from one ultrasound frame to the next but they may change within an ultrasound frame. This enables a rapid response to changes in bandwidth and would not be possible if the ultrasound frame data was converted into images and transmitted using MPEG, which requires the same number of pixels per picture.

It may be that when the number of scan positions per unit of measurement time in respect of which compressed ultrasound frame data is transmitted is regulated (e.g. reduced), the number of scan positions per unit of measurement time in respect of which ultrasound echoes are generated is not changed (e.g. reduced).

It may be that some ultrasound frame data, for example the ultrasound line data relating to a subset of lines, or the measurements of echoes from a subset of the scan positions in respect of which measurements are taken, is not transmitted in compressed form, for example, it may not be compressed and transmitted, or it may be compressed and not transmitted. For example, data concerning a subset of independently compressed scan lines may be discarded.

However, it may be that the ultrasound scanner is configured to regulate (e.g. reduce) the number of scan positions per unit of time which are scanned (i.e. in respect of which ultrasound pulses are focussed on), typically responsive to a received variable relating to a transmission property of the wireless transmitter. This will thereby regulate (e.g. reduce) the number of scan positions per unit of measurement time of the ultrasound frame data which is transmitted by the wireless transmitter, in compressed form. The method may comprise receiving a variable relating to a transmission property of the wireless transmitter and varying (e.g. reducing) the number of scan positions per unit of time upon which ultrasound pulses are focussed responsive thereto (typically by reducing the number of scan lines which are scanned per unit of time). This again regulates (e.g. reduce) the number of scan positions per unit of measurement time of the ultrasound frame data which is transmitted by the wireless transmitter, in compressed form.

This has the advantage of not only reducing the amount of data which is generated for transmission, and thereby maintaining image quality and or avoiding excessive latency, it also has the advantage of reducing the rate at which ultrasound pulses are generated and thereby reduces power consumption.

The number of scan positions per unit of time which are scanned may be regulated (e.g. reduced) by:
  regulating (e.g. reducing) the number of scan positions per scan line;
  regulating (e.g. reducing) the number of scan lines per ultrasound frame;
  regulating (e.g. increasing) the period between ultrasound frames.

It may be that the number of scan positions per unit of time which are scanned is varied (e.g. reduced) progressively (responsive to measurements of the variable relating to a transmission property of the wireless transmitter) through a plurality of different modes, which differ in terms of the number of scan positions which are scanned, in a predetermined order. The modes may differ in terms of one or more of: the number of scan positions per scan line, the number of scan lines per ultrasound frame and/or the period between ultrasound frames.

The ultrasound scanner typically comprises (or is in the form of) a handheld ultrasound probe, i.e. an ultrasound probe configured to be used while held in a single hand by a user. Thus, the ultrasound scanner may comprise an ultrasound probe including the ultrasound probe region. In this case the ultrasound scanner typically also comprises an ultrasound scanner body to which the ultrasound probe is connected in use (e.g. through a cable). The ultrasound scanner may comprise an integral body which is handheld and comprises the ultrasound probe region. Typically, the ultrasound scanner comprises one or more batteries. Typically the ultrasound scanner is powered only by the one or more batteries in operation. Power consumption is an important consideration in ultrasound scanners powered only by one or more batteries within the scanner.

The ultrasound scanner typically comprises a controller which regulates the rate at which scan positions are scanned. The ultrasound scanner typically comprises at least one processor and memory which stores a program which causes the at least one processor to function as the controller when executed. The transmit circuitry, the receive circuitry, the beam former and/or the data compressor may be formed in whole or in part by the processor executing a program stored in the memory. Dedicated transmit circuitry, receiver circuitry and beam former ICs are known in the art.

The ultrasound data processor typically comprises one or more processors and memory storing program code. The ultrasound data processor may be a handheld electronic device, for example a smartphone, tablet or laptop. The image display may be in wired communication with the image processor. However, the image display may be in wireless communication with the image processor, for example the image display may comprise video glasses in wireless communication with the image processor. The data decompressor and/or image processor may be implemented in whole or in part by a microprocessor of the ultrasound data processor executing program code stored in a memory. The image processor may be implemented in whole or in part by a graphic processor.

One skilled in the art will appreciate that although the one or more ultrasound sources and receivers may comprise one or more ultrasound sources and one or more separate ultrasound receivers, the one or more ultrasound sources and receivers may comprise one or more ultrasound transducers (e.g. an array of ultrasound transducers or one or more ultrasound transducers swept repetitively along a path during use), for example piezoelectric transducers or capacitive transducers, which function as both ultrasound sources and receivers.

Preferably, the time lag between ultrasound echoes being received by the ultrasound receivers and the final (remote) display of the ultrasound image calculated by processing measurements of those ultrasound echoes is less than 0.2 seconds or less than 0.1 seconds.

Preferably, the time lag between ultrasound echoes being received by the ultrasound receivers and the final (remote) display of the ultrasound image calculated by processing measurements of those ultrasound echoes is less than 6 times, and more preferably less than 3 times the period between ultrasound frames.

The apparatus and method may be used to scan a region of an animal, typically a non-human animal, for example a farm animal (e.g. a pig, horse, cow or sheep) or a domestic animal (e.g. a cat or a dog).

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
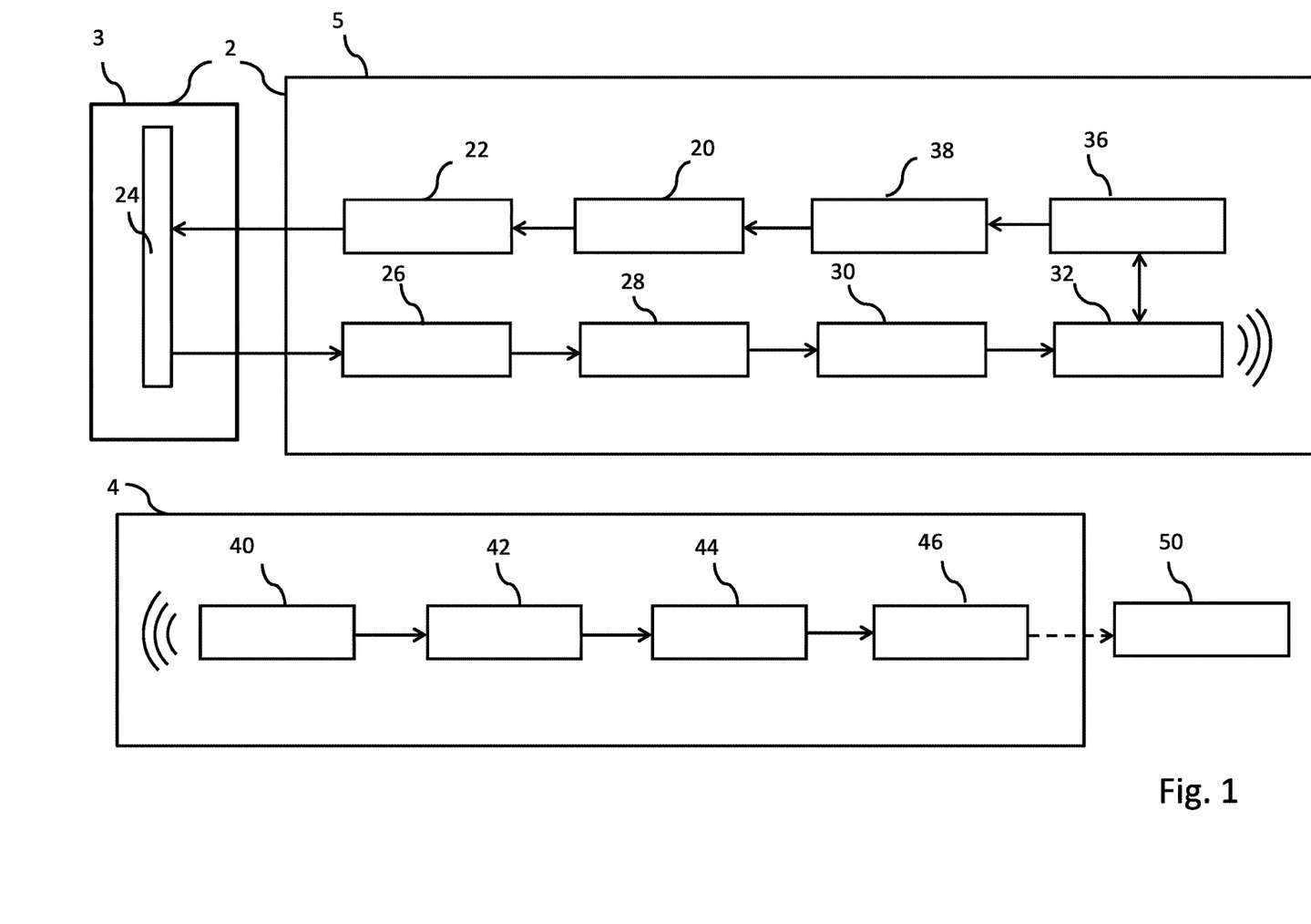
FIG. 1 is a block diagram of ultrasound apparatus.
Figure 2:
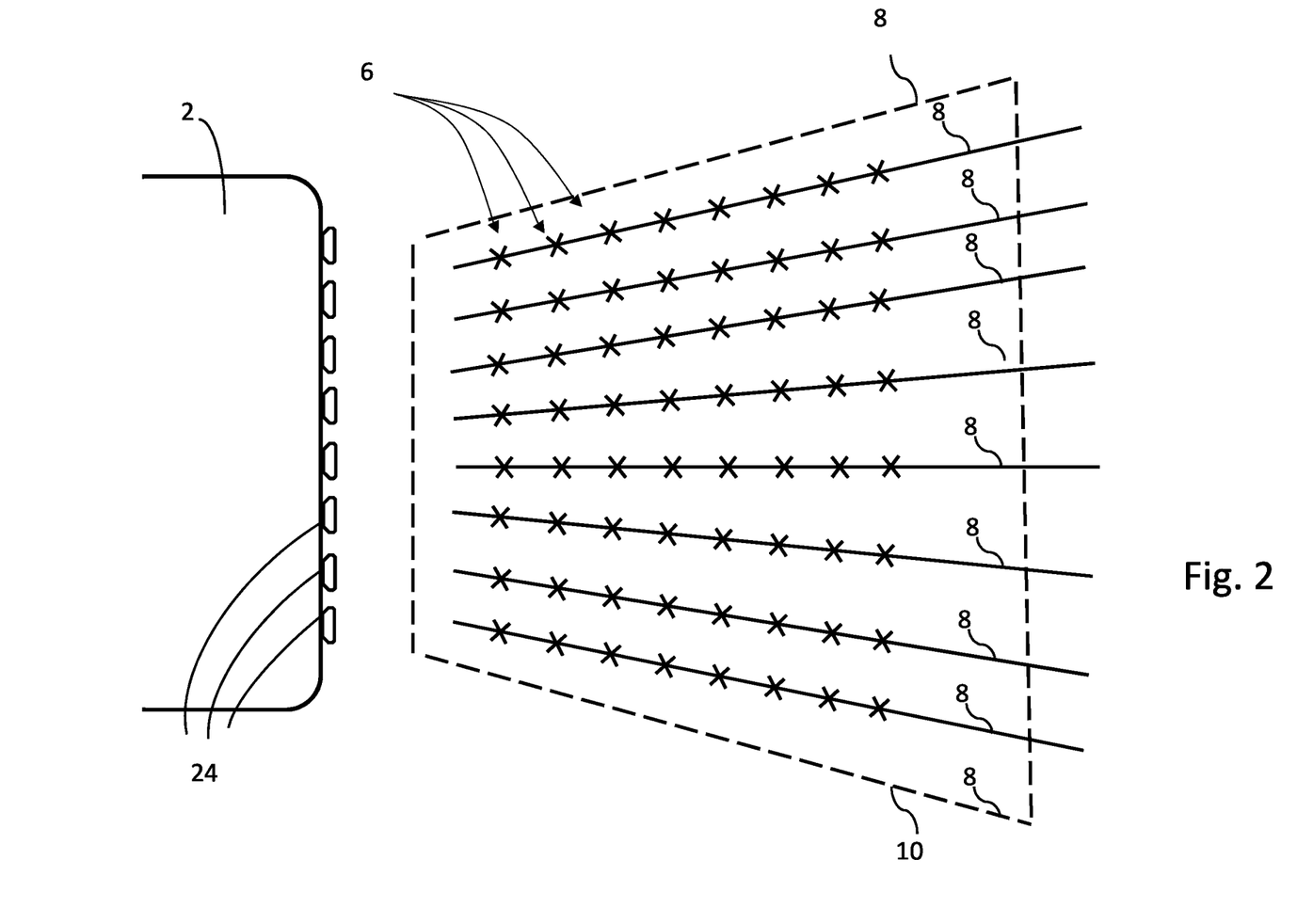
FIG. 2 is a schematic diagram of scan positions located along scan lines within a scan region.

With reference to FIGS. 1 and 2, ultrasound scanning apparatus according to the invention comprises a handheld ultrasound scanner 2 and a separate ultrasound data processor 4, which may be a dedicated computing device or a smart phone or tablet running a suitable application program, such as an iPhone, iPad or other iOS device (iPhone, iPad and iOS are trade marks of Apple Inc.) or a mobile telephone or tablet executing the Android operating system (Android is a trade mark of Google Inc.).

In the example shown in FIG. 1, the ultrasound scanner 2 comprises a body 5 and a separate ultrasound probe 3 which is connected to the body by a detachable cable. However, in some embodiments, the ultrasound scanner is a single integral unit (having a single casing) functioning as an ultrasound probe.

The ultrasound data processor has a display screen 50. The ultrasound data processor may be a single unit, however its functionality may be distributed between a plurality of units or devices. In some embodiments video generated by the ultrasound data processor is additionally or alternatively displayed on a remote display, for example on goggles worn by a user. The apparatus is used to generate ultrasound images of a scan region of an animal and to display these images to the user in real time so that the user can rapidly and accurately carry out a scanning task.

The ultrasound scanner 2 comprises a microprocessor executing a stored program, functioning as a controller 20. The controller regulates the scanning procedure, subsequent data processing and transmission. The ultrasound scanner has a one-dimensional (curved or straight line) array of ultrasound transducers 24, within the ultrasound probe (functioning as the ultrasound probe region), and a transmit beamformer 22 (comprising the transmit circuitry) which generates electrical signals in use to drive the ultrasound transducers to generate ultrasound pulses focussed in turn on specific scan positions 6 as they travel along scan lines 8 within a scan region 10.

The scanner further comprises a receive beamformer 26 (the beam processor, comprising the receive circuitry) configured to extract ultrasound pulse echoes from measurements made by the ultrasound transducers and a beamformed data processor 28 configured to carry out standard data processing steps on raw ultrasound data such as bandpass filtering, detection and log compression.

A compressor module 30 is configured to receive and compress ultrasound frame data output by the beamformed data processor and there is a Wi-Fi transceiver 32 (functioning as the wireless transmitter), having a transmit buffer 34, for transmitting compressed data from the compressor module in use. The scanner includes an internal (replaceable or integral) battery (optional rechargeable) which supplies all of the power to the scanner during use. The scanner may also have an interface for receiving power from an external source (e.g. a power cable) but external power sources may often be unavailable.

The ultrasound data processor 4 comprises a Wi-Fi transceiver 40 (functioning as the wireless receiver) and a decompression module 42 configured to decompress compressed ultrasound frame data received from the Wi-Fi transceiver. Wi-Fi is a wireless radio transmission protocol specified by the IEEE 802.11 standards. (Wi-Fi is a trade mark of the Wi-Fi Alliance).

An image processor 44 is provided to calculate ultrasound image data from the ultrasound frame data and is in electronic communication with a display interface 46 which transmits images to the display screen 50 in use for display.

One skilled in the art will appreciate that the extent to which the functionality of the components of the ultrasound scanner and ultrasound data processor are implemented as standalone circuits or as program code instructions executed by the microprocessor is a matter of design choice. For example, the compressor and decompressor might be implemented by the microprocessor executing program code or with dedicated circuits. The transmit beamformer, receive beamformer and Wi-Fi transceivers include dedicated circuitry but may be implemented in part by the microprocessor.

In embodiments in which the ultrasound scanner comprises both a body 5 and an ultrasound probe 3 the distribution of the components shown in FIG. 1 between the body and probe is a matter of design choice. Some or all of the transmit and receive circuitry, for example, may be in the ultrasound probe along with the transducers.

Figure 3:
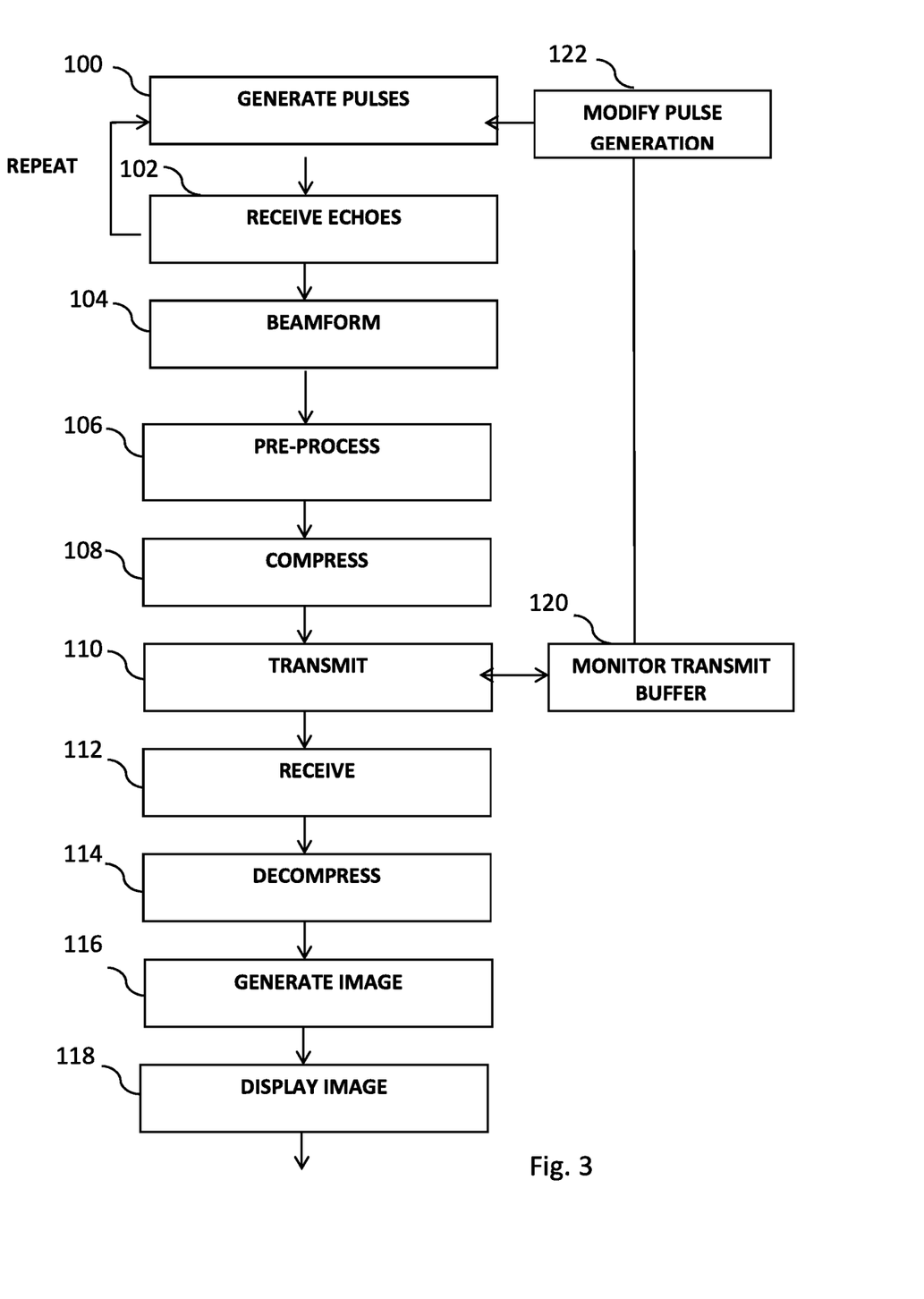
FIG. 3 is a flow diagram of an ultrasound apparatus operating procedure.

With reference to FIG. 2, during operation the controller 20 regulates the transmit beamformer to generate 100 ultrasound pulses which are focussed in turn on scan positions 6 spaced apart along the length of scan lines 8 in the scan region 10. Ultrasound echoes are received 102 by the ultrasound transceiver array and beamformed 104. The controller regulates the rate at which ultrasound frames are scanned, the number of scan lines in each ultrasound frame and the number of scan positions in each scan line. One skilled in the art will be aware of standard ultrasound techniques for controlling transmit and receive beamformers to scan the scan positions.

Thus, the ultrasound scanner transmits ultrasound pulses from a number of transducers, progressively along individual scan lines, and repeats the process to scan line across the scan region which is effectively a slice through a region of interest. The process is then repeated to rescan the region of interest. The data concerning each scan through the region of interest is an ultrasound frame.

The beamformed data is processed 106 by the beamformed data processor 28. This signal processing step includes data processing steps which are typically carried out on raw beamformed ultrasound measurement data such as band-pass filtering, detection and log compression. The beamformed data processor processes data concerning individual frames one at a time and within each frame processes data concerning individual scan lines one at a time.

Figure 4:
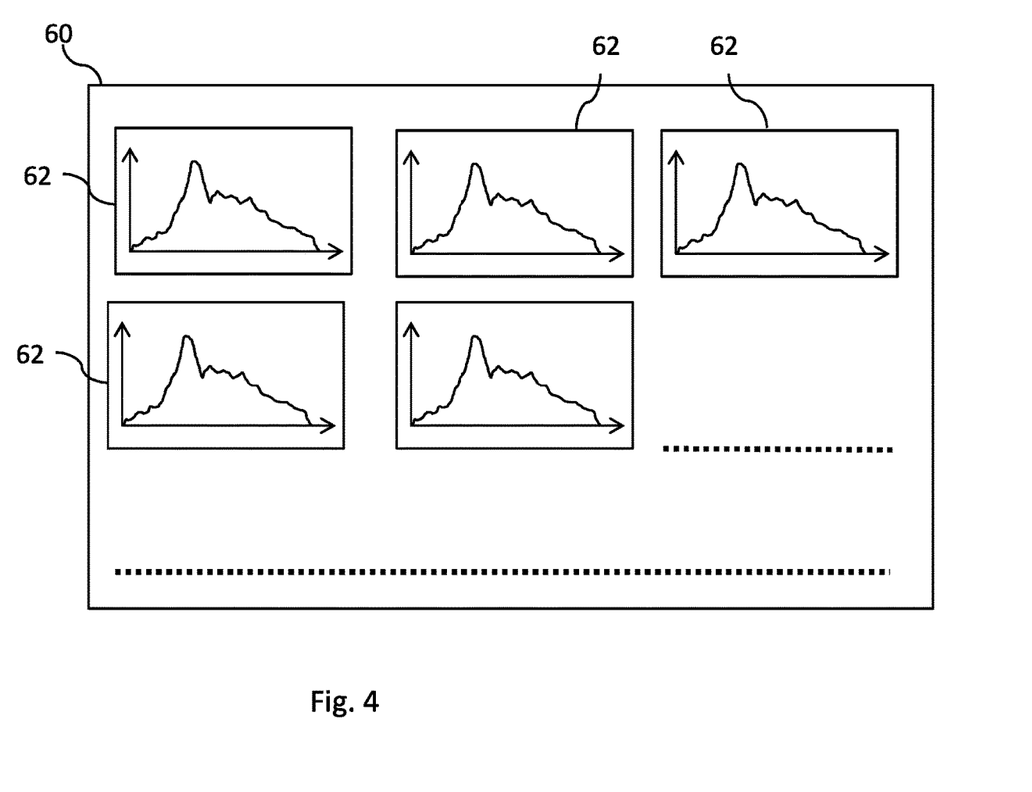
FIG. 4 is a block diagram of ultrasound frame data.

The output from the beamformed data processor is ultrasound frame data 60, which comprises a plurality of scan line data structures 62. Each scan line data structure relates to echoes received at different depths within individual scan lines. In this example, the scan line data is a measurement of echo brightness with depth (z) in a specific scan line. The scan line data structure also includes meta-data indicating to which slice the measurement data relates, for example it may specify an x and y position (relative to the transceiver array), angle, line length and number of scan points and/or distance between scan points. The scan lines are typically grouped in data structures concerning individual ultrasound frames, although this is not essential.

The data compression module compresses 110 the ultrasound frame data. In this example, the scan line data structures are processed in turn. The difference between consecutive measurements within the scan line data structure is calculated and then a variable length coding algorithm (such as Huffman coding, Lempel-Ziv coding or arithmetic coding) is used to encode those differences. We have found that, due to typical spatial variation of ultrasound echo intensities, this compression approach is efficient. In this example, the data concerning individual scan lines are compressed individually, i.e. the compressed data comprising data structures representing individual scan lines without reference to other scan lines. Furthermore, the compressed data relating to individual ultrasound frames represents individual ultrasound frames without reference to previous ultrasound frames. Meta-data need not be compressed. Using a 6-bit Huffman type variable length coding algorithm we have obtained data compression of about 50%.

Data generated by the data compression module is passed to the Wi-Fi module for wireless transmission 110 to the image processor. The compressed data is stored in the transmit buffer of the Wi-Fi module until it is transmitted. The compressed data is received 112 by the Wi-Fi module of the image processor.

The decompression module 42 then decompresses the received ultrasound frame data, by reversing the variable length encoding process to recreate the ultrasound frame data. Typically, the compression and decompression process is lossless and the ultrasound frame data can be faithfully reproduced, however it is not essential that this procedure is lossless.

The image processing module 44 then processes the decompressed ultrasound frame data and carries out typical ultrasound image generation procedures 116 known to the person skilled in the art, such as scan conversion, angle compounding frame smoothing, boundary/edge detection and so forth, and generate pictures, being individual image frames for consecutive display on a display 46 of the image processor. The image processor may be the microprocessor which functions as the controller (the CPU of the device) however video processing may be carried out with a dedicated graphics processing unit, for example using OpenGL with individual scan lines represented as OpenGL polygons.

The resulting images are then displayed on the display screen 50 or output through a video output interface (typically to a remote display screen, e.g. wirelessly). The images are displayed in real time, within 0.25 s of the ultrasound measurements which gave rise to the images. The user can therefore manoeuvre the ultrasound probe region (which may be involve manoeuvring the ultrasound scanner as a whole if it is integral, or simply manoeuvring an ultrasound probe) to view a region of interest of an animal.

We have found that this variable data rate can enable higher resolution images to be prepared when a given wireless data transmission bandwidth permits but in particular it enables video images to be maintained with reasonable latency even if the bandwidth of the Wi-Fi connection is sub-optimal. This makes the invention especially useful in a veterinary context where ultrasound images may need to be obtained in uncontrolled environments, such as outdoors or in farm buildings.

Still further, the controller includes a buffer monitor 36, which is typically program code executed periodically by the microprocessor or event triggered, which monitors the Wi-Fi buffer determines when the amount of data stored in the Wi-Fi transmit buffer 34 exceeds a threshold. This indicates that the bandwidth of the Wi-Fi transmission has decreased.

When that occurs, the controller changes the rate of scanning to reduce the rate at which scan data is generated by one or more of:
  Reducing the number of scan positions in each scan line (e.g. omitting every alternate scan position)
  Reducing the number of scan lines (e.g. omitting alternate scan lines)
  Reducing the number of scan lines which are scanned during each frame (e.g. scanning a scan line at a particular orientation during only some frames)
  Reducing the frame rate.

Thus, the rate at which scan data is generated is reduced. Typically the controller has a predefined priority order in which it proceeds through the different data reduction operations set out above if the transmit buffer size continues to increase. This has the side-effect of reducing power consumption by the ultrasound transmit circuitry.

In some embodiments, the rate of scanning is maintained but instead the measured ultrasound frame data is processed to omit (e.g. delete, not copy or not process) data concerning some (e.g. alternate) scan positions, or some (e.g. alternate) scan lines, or even to omit entire ultrasound frames without reducing the rate of scanning. This would not however reduce the power consumption of the ultrasound transmit circuitry.

The image processor can adapt to a reduction in the number of scan points in each line or number of scan lines by reducing the resolution of an image. If some or all scan points or scan lines are only included in some (e.g. alternate) ultrasound frames, the image processor can adapt to this by retaining values of the strength (e.g. intensity, amplitude or brightness) of ultrasound echoes from a scan location until further data concerning that scan location is received. If data concerning specific scan points, or scan lines is no longer available, the calculated resolution of the images concerning those scan points can be reduced or the strength of ultrasound echoes from the respective scan points or scan lines can be estimated by interpolation.

Furthermore, the rate of scanning can be reduced within an ultrasound frame. This allows a rapid response to changes in wireless transmission bandwidth or rapid recovery from intermittent data loss. If data is not received for a scan point or scan line, the previous values of ultrasound echo strength used by the image processor for that location may persist for a period of time, or may be estimated by interpolation.

In an example, in a default mode when there is sufficient Wi-Fi bandwidth, each frame comprises 128 scan lines with 480 scan positions per line, the measurement for each sample is represented as an 8 bit number; and there are 30 frames per second. Accordingly about 14 Mb/s of ultrasound frame data is generated. This is compressed to below 10 Mb/s and transmitted to the ultrasound data processor with a latency of below 0.1 seconds. If the transmit buffer begins to fill up, the number of scan positions per line might be reduced (e.g. to 240 then 120), the number of scan lines can be reduced (e.g. to 64) and the scan rate can be reduced (e.g. to 15 frames per second), reducing the transmit rate requirement to less than 1 MB/s. On the other hand, if images were generated by the ultrasound scanner and transmitted as MPEG compressed video, a minimum of 6 Mb/s would be required, there would be a latency of around 0.3 seconds as groups of 10 pictures would be encoded together and the video images would stop entirely, skip images or suffer substantial latency if there were intermittent reductions in Wi-Fi transmission rate.

However, using the methods of the present invention we have obtained a lag of as low as 70-90 milliseconds. For example, in an example with a time between ultrasound frames of 40 mS, plus transmit time of 3 mS transmitting a 5 GHz/18 mS transmitting at 2.4 GHz plus processing time (e.g. 20 mS) and time to render (10 mS) we have achieved a lag of 73 mS (transmitting at 5 GHz) or 88 mS (transmitting at 2.4 GHz) and images have continued to be updated continuously, possibly with a reduction in image quality, despite environmental variations affecting transmission rate which would have lead to gaps in the image stream transmitted by MPEG through the same bandwidth.

The invention claimed is:

1. Ultrasound imaging apparatus comprising an ultrasound scanner and a separate ultrasound data processor:
    the ultrasound scanner comprising:
        one or more ultrasound sources and receivers,
        transmit circuitry configured to apply electrical signals to the ultrasound sources to transmit ultrasound pulses into a scan region,
        receive circuitry configured to measure ultrasound echoes received at the ultrasound receivers from the scan region,
        a beam processor configured to process the measured ultrasound echoes and output ultrasound frame data, the ultrasound frame data comprising measurements of ultrasound echoes from each of a series of scan positions in the scan region,
        a data compressor configured to process ultrasound frame data output by the beam processor to generate compressed ultrasound frame data, and
        a wireless transmitter configured to wirelessly transmit the compressed ultrasound frame data;
    the ultrasound data processor comprising:
        a wireless receiver configured to receive the compressed ultrasound frame data transmitted by the wireless transmitter,
        a data decompressor configured to decompress compressed ultrasound frame data received by the wireless transmitter,
        an image processor configured to process decompressed data output by the data decompressor to form ultrasound images of the scan region, and
        a display interface wherein
        the ultrasound frame data comprises ultrasound line data portions which specify the measured strength of ultrasound echoes received by one or more ultrasound receivers from a series of spaced apart positions along a line and the data compressor is configured to output compressed ultrasound frame data in which each individual ultrasound line is compressed separately.

2. Ultrasound imaging apparatus according to claim 1, wherein the data compressor is configured to output compressed ultrasound frame data in which each individual ultrasound frame is compressed independently of any other frame.

3. Ultrasound imaging apparatus according to claim 1, wherein the data compressor is configured to calculate and encode the differences between consecutive measurements within ultrasound line data portions.

4. Ultrasound imaging apparatus according to claim 1, wherein the data compressor is a variable length code compressor.

5. Ultrasound imaging apparatus according to claim 1, wherein the ultrasound scanner is configured to regulate the number of scan positions per unit of measurement time of the ultrasound frame data which is transmitted by the wireless transmitter, in compressed form, responsive to a received variable relating to a transmission property of the wireless transmitter.

6. Ultrasound imaging apparatus according to claim 5, wherein regulating the number of scan positions per unit of measurement time of the ultrasound frame data which is transmitted by the wireless transmitter comprises one or more of:
    regulating the number of scan positions per scan line in respect of which compressed ultrasound frame data is transmitted;
    regulating the number of scan lines per ultrasound frame in respect of which compressed ultrasound frame data is transmitted; and
    regulating the period between ultrasound frames in respect of which compressed ultrasound frame data is transmitted.

7. Ultrasound imaging apparatus according to claim 6, wherein the number of scan positions per unit of time in respect of which compressed ultrasound frame data is transmitted is reduced progressively through a plurality of different modes, which differ in terms of the number of scan positions in respect of which compressed ultrasound frame data is transmitted, in a predetermined order, the modes differing in terms of one or more of: the number of scan positions per scan line, the number of scan lines per ultrasound frame and/or the period between ultrasound frames and wherein the apparatus is configured to vary the number of scan positions per unit of measurement time in respect of which data is transmitted within an ultrasound frame.

8. Ultrasound imaging apparatus according to claim 1, configured to regulate the number of scan positions per unit of time, responsive to a received variable relating to a transmission property of the wireless transmitter.

9. Ultrasound imaging apparatus according to claim 8, configured to regulate the number of scan positions per unit of time which are scanned by:
  regulating the number of scan positions per scan line;
  regulating the number of scan lines per ultrasound frame;
  regulating the period between ultrasound frames.

10. Ultrasound imaging apparatus according to claim 9, configured to regulate the number of scan positions per unit of time which are scanned progressively through a plurality of different modes, which differ in terms of the number of scan positions which are scanned, in a predetermined order, the modes differing in terms of one or more of: the number of scan positions per scan line, the number of scan lines per ultrasound frame and/or the period between ultrasound frames.

11. Ultrasound imaging apparatus according to claim 5, wherein the received variable relating to a transmission property of the wireless transmitter is a measurement related to the amount of data in a transmit buffer of the wireless transmitter.

12. Ultrasound imaging apparatus according to claim 1, wherein the time lag between ultrasound echoes being received by the ultrasound receivers and the display of the ultrasound image calculated by processing measurements of those ultrasound echoes is less than 0.2 seconds and/or is less than 5 times the period between ultrasound frames.

13. A method of processing ultrasound echo data to form images, the method comprising:
  at an ultrasound scanner comprising one or more ultrasound sources and receivers, receiving ultrasound echoes from a scan region,
    processing measurements of the received ultrasound echoes to thereby calculate ultrasound frame data, the ultrasound frame data comprising measurements of ultrasound echoes from each of a series of scan positions in the scan region,
    compressing the ultrasound frame data to generate compressed ultrasound frame data,
    transmitting the compressed ultrasound frame data through a wireless transmitter to a wireless receiver of an ultrasound data processor,
  at the ultrasound data processor, decompressing the received ultrasound frame data, processing the decompressed data to form ultrasound images of the portion of the subject, and outputting the ultrasound images,
  wherein the method comprises compressing each ultrasound line separately.

14. A method according to claim 13, wherein the compressed ultrasound frame data which is generated comprises data portions each of which represents an individual ultrasound frame compressed independently of any other frame.

15. A method according to claim 13, wherein the ultrasound frame data comprises ultrasound line data portions which specify the measured strength of ultrasound echoes received by one or more ultrasound receivers from a series of spaced apart positions along a line and the compressed ultrasound frame data comprises data portions each of which represents an individual ultrasound line without reference to any other ultrasound line data.

16. A method according to claim 13, wherein compressing the ultrasound frame data comprises applying a variable length code compression algorithm to the ultrasound frame data.

17. A method according to claim 13, comprising controlling transmit circuitry to apply electrical signals to the ultrasound sources to transmit ultrasound pulses into the scan region, and receiving a variable relating to a transmission property of the wireless transmitter and varying the number of scan positions per unit of measurement time of the ultrasound frame data which is transmitted by the wireless transmitter, in compressed form, responsive thereto, wherein regulating the number of scan positions per unit of measurement time of the ultrasound frame data which is transmitted by the wireless transmitter comprises one or more of:
  regulating the number of scan positions per scan line in respect of which compressed ultrasound frame data is transmitted;
  regulating the number of scan lines per ultrasound frame in respect of which compressed ultrasound frame data is transmitted; and
  regulating the period between ultrasound frames in respect of which compressed ultrasound frame data is transmitted.

18. A method according to claim 17, wherein the number of scan positions per unit of time in respect of which compressed ultrasound frame data is transmitted is reduced progressively through a plurality of different modes, which differ in terms of the number of scan positions in respect of which compressed ultrasound frame data is transmitted, in a predetermined order, the modes differing in terms of one or more of: the number of scan positions per scan line, the number of scan lines per ultrasound frame and/or the period between ultrasound frames and/or wherein the number of scan positions per unit of measurement time in respect of which data is transmitted is varied within an ultrasound frame.

19. A method according to claim 13, comprising regulating the number of scan positions which are scanned per unit of time, responsive to a received variable relating to a transmission property of the wireless transmitter, wherein the number of scan positions per unit of time which are scanned is regulated by:
  regulating the number of scan positions per scan line;
  regulating the number of scan lines per ultrasound frame;
  regulating the period between ultrasound frames.

20. A method according to claim 19, comprising varying the number of scan positions per unit of time which are scanned progressively through a plurality of different modes, which differ in terms of the number of scan positions which are scanned, in a predetermined order, the modes differing in terms of one or more of: the number of scan positions per scan line, the number of scan lines per ultrasound frame and/or the period between ultrasound frames.

* * * * *